US011166948B2

(12) United States Patent
Unno et al.

(10) Patent No.: US 11,166,948 B2
(45) Date of Patent: Nov. 9, 2021

(54) PHARMACEUTICAL COMPOSITION FOR TREATMENT OF AORTIC ANEURYSM

(71) Applicants: National University Corporation Hamamatsu University School of Medicine, Shizuoka (JP); Kowa Company, Ltd., Nagoya (JP)

(72) Inventors: Naoki Unno, Shizuoka (JP); Hiroki Tanaka, Shizuoka (JP); Tatsuro Yata, Shizuoka (JP); Keisuke Inoue, Tokyo (JP); Yuichi Makinose, Tokyo (JP); Noboru Kaneta, Tokyo (JP)

(73) Assignees: National University Corporation Hamamatsu University School of Medicine, Shizuoka (JP); Kowa Company, Ltd., Aichi (JP)

( * ) Notice: Subject to any disclaimer, the term of this patent is extended or adjusted under 35 U.S.C. 154(b) by 0 days.

(21) Appl. No.: 16/647,448

(22) PCT Filed: Sep. 13, 2018

(86) PCT No.: PCT/JP2018/033923
§ 371 (c)(1),
(2) Date: Mar. 13, 2020

(87) PCT Pub. No.: WO2019/054432
PCT Pub. Date: Mar. 21, 2019

(65) Prior Publication Data
US 2020/0215050 A1 Jul. 9, 2020

(30) Foreign Application Priority Data

Sep. 13, 2017 (JP) .............................. JP2017-175373
Oct. 16, 2017 (JP) .............................. JP2017-200093

(51) Int. Cl.
*A61K 31/4704* (2006.01)
*A61P 9/14* (2006.01)
*C07D 215/227* (2006.01)

(52) U.S. Cl.
CPC ............ *A61K 31/4704* (2013.01); *A61P 9/14* (2018.01)

(58) Field of Classification Search
CPC .... A61K 31/4704; A61P 9/14; C07D 215/227
See application file for complete search history.

(56) References Cited

U.S. PATENT DOCUMENTS 6,143,763 A  11/2000  Koga et al.
2014/0330022 A1  11/2014  Yoshida et al.

FOREIGN PATENT DOCUMENTS

JP  2015-178460 A  10/2015
WO  97/12869 A1  4/1997
WO  2013/103148 A1  7/2013

OTHER PUBLICATIONS

Zhang, Q. et al., Journal of Surgical Research, 2011, vol. 167, pp. e385-e393.
Umebayashi, R. et al., 2012, p. 252, ISSN 1347-7099, p. 127, non-official translation (Programs and abstracts of the 44th general conference of Japan Atherosclerosis Society)
Koga, y. et al., Bioorganic & Medicinal Chemistry Letters, 1998, vol. 8, pp. 1471-1476, ISSN 0960-894X, in particular, abstract, table 2.
Tanaka, H. et al., PLoS One, 2015, ol. 10, No. 8, e0134386, pp. 1-23, ISSN 1932-6203.
Senemaud, J. et al. Arterioscler Thromb Vasc Biol., DOI:10.1161/ATVBAHA.116.308534, 2017.
Gollege, J. et al., Atherosclerosis 210 (2010) 51-56.
Kugo, H. et al., Scientific Reports |6:31268| DOI: 10-1038/srep31268 dated Aug. 8, 2017.
Ikenoya, M., et al., Biochemical and Biophysical Research Communications 353 (2007) 1111-1114.
International Search Report cited in PCT/JP2018/033923,dated Dec. 18, 2018.
Inoue et al., "Effects of canagliflozin on body composition and hepatic fat content in type 2 diabetes patients with non-alcoholic fatty liver disease", Journal of Diabetes Investigation, Jul. 2019;10(4):1004-1011 doi: 10.1111/jdi.12980. Epub Jan. 4, 2019.
Supplementary European Search Report dated May 7, 2021: EP 18857283.8.

*Primary Examiner* — Brenda L Coleman
(74) *Attorney, Agent, or Firm* — Mintz Levin Cohn Ferris Glovsky and Popeo, P.C.; Peter F. Corless; Joohee Lee (57) ABSTRACT

The present invention addresses the problem of providing a therapeutic agent for abdominal aortic aneurysms, with which pharmacotherapy is possible.
The present invention provides a therapeutic agent for an aortic aneurysm comprising, as an active component, (−)-6-[3-[3-cyclopropyl-3-[(1R,2R)-2-hydroxycyclohexyl]ureido]propoxy]-2(1H)-quinolinone or a salt thereof, or a solvate of these.

22 Claims, 4 Drawing Sheets

PHARMACEUTICAL COMPOSITION FOR TREATMENT OF AORTIC ANEURYSM

CROSS-REFERENCES TO RELATED APPLICATIONS

This application is a 35 U.S.C. § 371 U.S. national entry of International Application PCT/JP2018/033923, having an international filing date of Sep. 13, 2018, which claims under 35 U.S.C. § 119 the benefit of Japanese Patent Application 2017-200093, filed on Oct. 16, 2017 and Japanese Patent Application 2017-175373, filed on Sep. 13, 2017. The entire contents of these applications are incorporated herein by reference in their entirety.

TECHNICAL FIELD

The present invention relates to a therapeutic composition for aortic aneurysms comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof. In particular, it relates to a pharmaceutical composition for the treatment of an abdominal aortic aneurysm.

BACKGROUND ART

An aortic aneurysm is defined as "a state in which part of an aortic wall dilates or protrudes (in diameter) whole circumferentially or locally". When part of the aortic wall dilates locally to form an aneurysm, or the diameter dilates to more than 1.5 times the normal diameter (45 mm for the thorax and 30 mm for the abdomen) (dilates in the form of a fusiform or sac), the state is called "aneurysm". The incidence of annual onset in Japan has been reported to be about 3 per 100,000 population, but according to the statistics of the Japanese Association for Thoracic Surgery, the number of aortic aneurysm surgery cases is increasing year by year.

Aortic aneurysms are classified depending on the form of their aneurysm wall, the location of the aneurysm, the cause, the shape of the aneurysm, or the like.

Aortic aneurysms are classified into true, false, and dissecting, depending on the form of their aneurysm wall.

Aortic aneurysms are classified into thoracic, thoracoabdominal, and abdominal, depending on the location of the aneurysm.

Aortic aneurysms are classified into atherosclerotic, traumatic, inflammatory, infectious, and congenital, depending on the cause.

In addition, depending on the shape of the aneurysm, aortic aneurysms are classified into fusiform type and saccular type.

An abdominal aortic aneurysm (hereinafter also referred to as "AAA") is a disease in which the aortic wall becomes fragile and dilates to 1.5 times or more the normal diameter (AAA maximum short-axis diameter: more than 30 mm), and the mortality rate when rupture occurs is said to be 50% to 90%. The rupture rate (%/year) of AAA is almost 0%/year when the AAA maximum short-axis diameter is about 30 mm, but it increases as the diameter increases, and when the diameter exceeds 70 mm, it is said to be 20% to 40%/year. The only treatment option for AAA with increased rupture potential is surgery to prevent aneurysm rupture by aortic aneurysmectomy (blood vessel prosthesis implantation) or endovascular stent-grafting, and pharmacotherapy has not been established yet. Although the measure for implementation of surgery is an AAA maximum short-axis diameter of more than 50 mm or at least 5-mm dilatation within half a year (reference: http://www.j-circ.or.jp/guideline/pdf/JCS2011_takamoto_d.pdf), AAA is a disease that is common in older adults, and cannot be treated in patients who cannot choose blood vessel prosthesis implantation that requires laparotomy due to their general state or who cannot be treated with stent grafts due to morphological restrictions of an aortic aneurysm. Therefore, the development of a therapeutic agent for AAA by preventing or suppressing aneurysm rupture is strongly desired. A therapeutic agent effective for medical treatment not only of abdominal aortic aneurysms but also of general aortic aneurysms is strongly desired.

Regarding the development of therapeutic agents for AAA, studies using animal models such as APO-E-deficient mice, Angiotensin II continuous administration (Ang II)-induced models, elastase-induced models, calcium chloride ($CaCl_2$)-induced models are known. However, after confirming the effectiveness in these animal models, no drug has been able to further demonstrate the effectiveness in clinical trials. As a result, there is no clinically available therapeutic agent to date.

The above facts may also suggest the limitation of these animal models themselves. In other words, these animal models are those in which, among the intima, media, and adventitia that constitute the blood vessel wall, arteriosclerosis of the intima is caused or inflammation of the media is externally induced to form an aneurysm, and the aortic aneurysm thus induced merely constitutes part of the pathology of human AAA. That is, it cannot necessarily be said that these animal models faithfully reflect the pathology of the human aortic aneurysm. Specifically, many differences from human AAA are considered to be problematic, for example, aortic aneurysms do not rupture (elastase-induced or $CaCl_2$-induced model), the maximum short-axis diameter does not continuously dilate (AngII-induced, elastase-induced, or $CaCl_2$-induced model), and intraluminal thrombi do not adhere within the walls of aortic aneurysms (AngII-induced or $CaCl_2$-induced model) (Non-Patent Document 1).

Among the existing models, the AngII-induced model leads to rupture. However, in this model, an aneurysm is formed in the aortas in the thorax and just below the diaphragm rather than in the abdomen, so, considering that most of human AAA occurs in the aortas below the renal artery branch, the AngII-induced model does not directly mimic human AAA. Also, unlike human AAA in which part of an aortic wall dilates (or protrudes), this model presents an aortic dissection phenotype in which the aortic wall is separated into two layers and formed into two cavities along the artery running. Therefore, there are also differences in pathology. Therefore, the AngII-induced model cannot be said to be appropriate as an experimental model for evaluating AAA rupture. In addition, there are cases (Non-Patent Document 2) where the rupture could not be suppressed even when the aneurysm dilatation induced in the model animal was suppressed. Therefore, as far as the existing models are referred to, the suppression of AAA dilatation cannot always lead to suppress AAA rupture.

Under these circumstances, it has been found from the histopathological observation of human AAA that the AAA wall is ischemic and hypoxic due to the stenosis of vasa vasorum (VV), a microvessel that controls blood flow in the aortic wall. A new animal model that presents an AAA histopathological phenotype more approximate to the human AAA histopathological phenotype by inducing VV hypoperfusion and hypoxia in the aortic walls has been newly developed (Non-Patent Document 3). The aortic aneurysm histopathological phenotype of this model reproduces the intimal thickening and medial degeneration of the arterial wall, as well as the increase in intraluminal thrombi and increase in adventitial adipocytes, which are not observed in conventional animal models. Therefore, the relationship between AAA rupture and vascular wall adipocyte generation is demonstrated (Non-Patent Document 4). By using this model created from a rat (hereinafter sometimes referred to as "aortic wall hypoxia-induced rat AAA model"), it is considered that this model can be used to evaluate the effects of drugs more appropriately than the conventional models.

Meanwhile, (−)-6-[3-[3-cyclopropyl-3-[(1R,2R)-2-hydroxycyclohexyl]ureido]propoxy]-2(1H)-quinolinone (hereinafter sometimes referred to as "Compound 1") have antiplatelet action, antithrombotic action and PDE3 inhibitory action. Applicable scope of the compound includes brain diseases such as cerebral atherosclerosis, cerebral infarction, transient cerebral ischemic attack, and recovery ischemic neurological deficit; heart diseases such as myocardial infarction and angina pectoris; chronic arterial occlusion such as Buerger's disease, obstructive arteriosclerosis, and intermittent claudication; diabetic complications such as diabetic neuropathy, diabetic skin ulcer, and diabetic nephropathy; and ischemic diseases such as prevention of restenosis after percutaneous transluminal coronary angioplasty (PTCA), directional coronary atherectomy (DCA) and stent intervention, and the like, prevention of re-occlusion after transplantation of artificial organs such as artificial blood vessels, and kidneys, and the like, and prevention of thrombi and emboli development after surgery, and during extracorporeal circulation such as kidney dialysis (Non-Patent Document 5 and Patent Document 1). However, it is not known that Compound 1 is effective for the treatment of aortic aneurysms, for example, treatment based on suppression of rupture or dilatation of abdominal aortic aneurysms.

Although it has been experimentally reported that cilostazol, a PDE3 inhibitor, suppresses AAA dilatation in elastase-induced model rats (Non-Patent Document 6), this paper reports that the formation and dilatation of aneurysms were suppressed by preventive administration of cilostazol before AAA formation, and is fundamentally different in viewpoint from the study on the effectiveness of administering a drug for therapeutic purposes after AAA formation. In the clinical practice, it is impossible to administer a drug to all humans in advance in order to prevent the formation of AAA. In addition, there is no drug which has been confirmed to be effective upon preventive administration as shown in Non-Patent Document 6, and has been able to suppress further dilatation upon therapeutic administration after aneurysm formation in human clinical studies. Furthermore, Non-Patent Document 6 does not show the possibility that cilostazol suppresses the rupture of AAA.

CITATION LIST

Patent Document

Patent Document 1: WO97/12869

Non-Patent Document

Non-Patent Document 1: Arterioscler. Thromb. Vasc. Biol. 2017 (March); 37 (3): 401-10

Non-Patent Document 2: Atherosclerosis 2010; 210 (1): 51-6

Non-Patent Document 3: PLoS ONE 2015; 10 (8): e0134386

Non-Patent Document 4: Sci. Rep. 2016; 6: 31268

Non-Patent Document 5: Biochem. Biophys. Research Commun. 2007; 353 (4): 1111-14

Non-Patent Document 6: J. Surg. Res. 2011; 167: e385-93

SUMMARY OF THE INVENTION

Problems to be Solved by the Invention

An object of the present invention is to provide a therapeutic composition for an aortic aneurysm, in particular, a therapeutic composition that suppresses the rupture and dilatation of an abdominal aortic aneurysm.

Means for Solving the Problems

As a result of intensive studies to solve the above-mentioned problems, the present inventors have found that Compound 1 suppresses rupture of an abdominal aortic aneurysm in an aortic wall hypoxia-induced rat AAA model, and further suppresses dilatation thereof, and completed the present invention.

Specifically, the present invention relates to a pharmaceutical composition for the treatment of an aortic aneurysm comprising, as an active ingredient, (−)-6-[3-[3-cyclopropyl-3-[(1R,2R)-2-hydroxycyclohexyl]ureido]propoxy]-2(1H)-quinolinone (Compound 1) or a salt, or a solvate, or a solvate of the salt thereof. More preferably, the present invention relates to a pharmaceutical composition for the treatment of an abdominal aortic aneurysm comprising, as an active ingredient, Compound 1 or a salt, or a solvate, or a solvate of the salt thereof. In a further preferred aspect, the treatment of an abdominal aortic aneurysm according to the present invention is suppression of aortic aneurysm rupture and/or suppression of dilatation of an aortic aneurysm, and the present invention relates to an agent for suppressing abdominal aortic aneurysm rupture and/or an agent for suppressing dilatation of an abdominal aortic aneurysm comprising, as an active ingredient, Compound 1 or a salt, or a solvate, or a solvate of the salt thereof. Here, the suppression of aortic aneurysm rupture can also be referred to as prevention of aortic aneurysm rupture. Therefore, the agent for suppressing (abdominal) aortic aneurysm rupture, which is one aspect of the present invention, can also be referred to as a prophylactic agent for (abdominal) aortic aneurysm rupture.

Moreover, the present invention relates to a pharmaceutical composition for the treatment for patients with aortic aneurysm after endovascular stent-grafting, as one preferable aspect. The pharmaceutical composition is used to treat an aortic aneurysm by rupture suppression, dilatation suppression, and/or size reduction. For example, the present invention relates to an agent for suppressing abdominal aortic aneurysm rupture after endovascular stent-grafting, comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof.

As another preferred aspect, the present invention relates to a pharmaceutical composition for the treatment for patients with aortic aneurysm before endovascular stent-grafting or aortic aneurysmectomy (blood vessel prosthesis implantation). At a stage before endovascular stent-grafting or aortic aneurysmectomy (blood vessel prosthesis implantation), the pharmaceutical composition of the present invention is used for the treatment of an aortic aneurysm (rupture suppression, dilatation suppression, and/or size reduction). For example, the present invention relates to an agent for suppressing abdominal aortic aneurysm rupture before endovascular stent-grafting or aortic aneurysmectomy (blood vessel prosthesis implantation), comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof.

That is, the present invention relates to use of (−)-6-[3-[3-cyclopropyl-3-[(1R,2R)-2-hydroxycyclohexyl]ureido]propoxy]-2(1H)-quinolinone or a salt, or a solvate, or a solvate of the salt thereof in the treatment of an aortic aneurysm. More specifically, the present invention relates to the following items [1] to [37].

[1] A pharmaceutical composition for the treatment of an aortic aneurysm comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof.

[2] The pharmaceutical composition according to above [1], wherein the treatment of the aortic aneurysm includes at least one treatment selected from the group consisting of suppression of aneurysm rupture, suppression of aneurysm dilatation, and aneurysm size reduction.

[3] The pharmaceutical composition according to above [1] or [2], wherein the treatment of the aortic aneurysm is suppression of aortic aneurysm rupture.

[4] The pharmaceutical composition according to above [1] or [2], wherein the treatment of the aortic aneurysm is suppression of dilatation of the aortic aneurysm.

[5] The pharmaceutical composition according to any one of above [1] to [4], which is used for patients with aortic aneurysm after endovascular stent-grafting.

[6] The pharmaceutical composition according to any one of above [1] to [4], which is used for patients with aortic aneurysm before endovascular stent-grafting or aortic aneurysmectomy (blood vessel prosthesis implantation).

[7] The pharmaceutical composition according to any one of above [1] to [6], wherein the aortic aneurysm is an abdominal aortic aneurysm.

[8] The pharmaceutical composition according to above [7], which is used for patients with abdominal aortic aneurysm having a maximum short-axis diameter of greater than 30 mm or greater than 40 mm.

[9] The pharmaceutical composition according to above [8], which is used for patients with abdominal aortic aneurysm having a maximum short-axis diameter of 50 mm or less.

[10] The pharmaceutical composition according to above [7] or [8], which is used for patients with abdominal aortic aneurysm having a maximum short-axis diameter of greater than 50 mm, greater than 60 mm, or greater than 70 mm.

[11] The pharmaceutical composition according to any one of above [1] to [10], which comprises a pharmaceutically acceptable carrier.

[12] A method for treating an aortic aneurysm, comprising a step of administering an effective amount of (−)-6-[3-[3-cyclopropyl-3-[(1R,2R)-2-hydroxycyclohexyl]ureido]propoxy]-2(1H)-quinolinone or a salt, or a solvate, or a solvate of the salt thereof to a subject in need of treatment, wherein the subject is a patient with aortic aneurysm selected from the group consisting of abdominal aortic aneurysms, thoracoabdominal aortic aneurysms, and thoracic aortic aneurysms.

[13] The method according to above [12], wherein the treatment needed is a treatment selected from the group consisting of suppression of aortic aneurysm rupture, suppression of aortic aneurysm dilatation, and aortic aneurysm size reduction.

[14] The method according to above [12] or [13], wherein treatment needed is suppression of aortic aneurysm rupture.

[15] The method according to above [12] or [13], wherein the treatment needed is suppression of aortic aneurysm dilatation.

[16] The method according to any one of above [12] to [15], wherein the subject is a patient with aortic aneurysm after endovascular stent-grafting.

[17] The method according to any one of above [12] to [15], wherein the subject is a patient with aortic aneurysm before endovascular stent-grafting or aortic aneurysmectomy (blood vessel prosthesis implantation).

[18] The method according to any one of above [12] to [17], wherein the subject is a patient with abdominal aortic aneurysm.

[19] The method according to above [18], wherein the subject is a patient with abdominal aortic aneurysm having maximum short-axis diameter of greater than 30 mm or greater than 40 mm.

[20] The method according to above [19], wherein the subject is a patient with abdominal aortic aneurysm having maximum short-axis diameter of 50 mm or less.

[21] The method according to above [18] or [19], wherein the subject is a patient with abdominal aortic aneurysm having maximum short-axis diameter of greater than 50 mm, greater than 60 mm, or greater than 70 mm.

[22] The method according to any one of above [12] to [21], wherein the (−)-6-[3-[3-Cyclopropyl-3-[(1R,2R)-2-hydroxycyclohexyl]ureido]propoxy]-2(1H)-quinolinone or a salt, or a solvate, or a solvate of the salt thereof is administered together with a pharmaceutically acceptable carrier.

[23] Use of (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for the manufacture of a pharmaceutical composition for the treatment of an aortic aneurysm.

[24] The use according to above [23], wherein the treatment of the aortic aneurysm includes at least one treatment selected from the group consisting of suppression of aneurysm rupture, suppression of aneurysm dilatation, and aneurysm size reduction.

[25] The use according to above [23] or [24], wherein the treatment of the aortic aneurysm is suppression of aortic aneurysm rupture.

[26] The use according to above [23] or [24], wherein the treatment of the aortic aneurysm is suppression of aortic aneurysm dilatation.

[27] The use according to any one of above [23] to [26], which is used for patients with aortic aneurysm after endovascular stent-grafting.

[28] The use according to any one of above [23] to [26], which is used for patients with aortic aneurysm before endovascular stent-grafting or aortic aneurysmectomy (blood vessel prosthesis implantation).

[29] The use according to any one of above [23] to [28], wherein the aortic aneurysm is an abdominal aortic aneurysm.

[30] The use according to any one of above [23] to [29], wherein the pharmaceutical composition comprises a pharmaceutically acceptable carrier.

[31] (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use in the treatment of an aortic aneurysm.

[32] The (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use according to above [31], wherein the treatment of the aortic aneurysm includes at least one treatment selected from the group consisting of suppression of aneurysm rupture, suppression of aneurysm dilatation, and aneurysm size reduction.

[33] The (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use according to above [31] or [32], wherein the treatment of the aortic aneurysm is suppression of aortic aneurysm rupture.

[34] The (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use according to above [31] or [32], wherein the treatment of the aortic aneurysm is suppression of aortic aneurysm dilatation.

[35] The (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use according to any one of above [31] to [34], wherein the treatment is treatment for patients with aortic aneurysm after endovascular stent-grafting.

[36] The (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use according to any one of above [31] to [34], wherein the treatment is treatment for patients with aortic aneurysm before endovascular stent-grafting or aortic aneurysmectomy (blood vessel prosthesis implantation).

[37] The (−)-6-[3-[3-cyclopropyl-3-[(1R,2R)-2-hydroxycyclohexyl]ureido]propoxy]-2(1H)-quinolinone or a salt, or a solvate, or a solvate of the salt thereof for use according to any one of above [31] to [36], wherein the aortic aneurysm is an abdominal aortic aneurysm.

The present invention also relates to the inventions described in the following items [A] to [G].

[A] An agent for the treatment of an aortic aneurysm comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof.

[B] The agent according to above [A], wherein the treatment of the aortic aneurysm includes at least one treatment selected from the group consisting of suppression of aneurysm rupture, suppression of aneurysm dilatation, and aneurysm size reduction.

[C] An agent for suppressing aortic aneurysm rupture comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof.

[D] The agent according to above [C], wherein the aortic aneurysm is an abdominal aortic aneurysm.

[E] The agent according to above [C] or [D], wherein the aortic aneurysm rupture is aneurysm rupture after endovascular stent-grafting.

[F] An agent for suppressing aortic aneurysm dilatation comprising, as an active ingredient, (−)-6-[3-[3-cyclopropyl-3-[(1R,2R)-2-hydroxycyclohexyl]ureido]propoxy]-2(1H)-quinolinone or a salt, or a solvate, or a solvate of the salt thereof.

[G] The agent according to above [F], wherein the aortic aneurysm is an abdominal aortic aneurysm.

Effects of the Invention

Compound 1 of the present invention, as will be illustrated in the Examples below, suppressed AAA rupture and improved the non-rupture survival rate in an aortic wall hypoxia-induced rat AAA model. Furthermore, the dilatation of the AAA diameter was suppressed in the aortic wall hypoxia-induced rat AAA model. Accordingly, the (−)-6-[3-[3-cyclopropyl-3-[(1R,2R)-2-hydroxycyclohexyl]ureido]propoxy]-2(1H)-quinolinone or a salt, or a solvate, or a solvate of the salt thereof according to the present invention can provide a novel medical treatment method for an aortic aneurysm typified by suppression of abdominal aortic aneurysm rupture and/or suppression of dilatation of the abdominal aortic aneurysm.

MODES FOR CARRYING OUT THE INVENTION

Compound 1 of the present invention is a known compound and can be manufactured by the method described in Patent Document 1 (WO97/12869) or a method conforming thereto.

In the present invention, a salt or a solvate of Compound 1 can also be used. The salt and solvate of Compound 1 can be manufactured by a conventional method.

The salt of Compound 1 of the present invention includes an addition salt with a base, and is not particularly limited as long as it is pharmaceutically acceptable. Examples of such salts include base addition salts with alkali metals such as potassium and sodium, and alkaline earth metals such as magnesium and calcium.

Examples of the solvate of Compound 1 of the present invention include hydrates and alcohol solvates (for example, ethanol solvates).

The agent for suppressing an abdominal aortic aneurysm rupture of the present invention suppresses AAA rupture, and thus prevents death from AAA rupture. Further, the agent can be applied for suppressing rupture of aortic aneurysms including thoracoabdominal aortic aneurysms and thoracic aortic aneurysms. It is useful as an agent for suppressing aortic aneurysm rupture before aortic aneurysmectomy (blood vessel prosthesis implantation), before or after endovascular stent-grafting. The pharmaceutical composition for the treatment of an aortic aneurysm of the present invention is preferably used as an agent for suppressing AAA rupture before or after endovascular stent-grafting. Furthermore, the dilatation suppressing action of the pharmaceutical composition for the treatment of an abdominal aortic aneurysm of the present invention suppresses AAA dilatation, and thus prevents death from rupture resulting from the AAA dilatation. In addition, the pharmaceutical composition of the present invention can also be applied for suppressing dilatation of aortic aneurysms including thoracoabdominal aortic aneurysms and thoracic aortic aneurysms. It is useful as an agent for suppressing aortic aneurysm dilatation before aortic aneurysmectomy (blood vessel prosthesis implantation), before or after endovascular stent-grafting. The pharmaceutical composition for the treatment of an aortic aneurysm of the present invention is preferably also used as an agent for suppressing AAA dilatation before or after endovascular stent-grafting.

Compound 1 of the present invention can be made, alone or in combination with any other pharmaceutically acceptable carrier such as a solubilizer, an excipient, a binder or a diluent, into a dosage form such as a tablet, a capsule, a granule, a powder, a lotion, an ointment, an injection or a suppository. These formulations can be manufactured by known methods. For example, in the case of a formulation for oral administration, a solubilizer such as tragacanth gum, gum arabic, sucrose ester, lecithin, olive oil, soybean oil, or PEG400; an excipient such as starch, mannitol, or lactose; a binder such as carboxymethylcellulose sodium or hydroxypropylcellulose; a disintegrant such as crystalline cellulose or carboxymethylcellulose calcium; a lubricant such as talc or magnesium stearate; a fluidity improver such as a light silicic anhydride; a diluent such as corn starch, and the like can be appropriately combined and formulated to manufacture the formulation.

Compound 1 of the present invention is administered orally or parenterally. The dose of Compound 1 of the present invention varies depending on the patient's body weight, age, sex, symptoms, etc., and can be appropriately set by those skilled in the art. For an adult, Compound 1 is preferably administered in an amount of usually 0.01 to 1000 mg, preferably 5 to 400 mg, more preferably 25 to 200 mg per day in 1 or 2 divided dose(s).

EXAMPLES

Hereinafter, the present invention will be described in more detail by way of Examples, but is not limited at all by these Examples.

Example 1: Action of Compound 1 in Aortic Wall Hypoxia-Induced Rat AAA Model The action of Compound 1 in a rat AAA model (Non-Patent Document 3) induced by operation in which the aortic wall was separated from the surrounding tissue, a catheter was inserted, and then the abdominal aorta was ligated together with a catheter with a thread was studied.

In this test, Compound 1 was manufactured according to the method described in Patent Document 1, and mixed, in a proportion of 0.15%, with a normal diet (FR2, manufactured by Funabashi Farm Co., Ltd.), and the Compound 1-mixed diet was used.

(1) Test Animal and Rearing Environment

Sprague-Dawley male rats (300 to 350 g: Japan SLC, Inc.) were used in the experiment. The rats were reared at room temperature of 25° C. ±1° C., and allowed to freely take the feed and water.

(2) Creation of Aortic Wall Hypoxia-Induced Rat AAA Model

The model was created according to the method described in Non-Patent Document 3. Specifically, a rat AAA model was created by separating the rat aortic wall from the surrounding tissue, inserting a polyurethane catheter, and then ligating the abdominal aorta together with a plastic catheter with a monofilament thread, and inducing AAA.

(3) Grouping and Drug Administration

The rat models were divided into two groups: a normal diet administration group (hereinafter referred to as "control group") (n=20) and a 0.15% Compound 1-mixed diet administration group (hereinafter referred to as "Compound 1 group") (n=20). The normal diet or Compound 1-mixed diet was freely fed in a period from one week before the AAA model creation operation (7 days before operation) to the end of the experiment.

(4) Observation and Inspection Method

In both the groups, up to 28 days post operation, the aneurysm diameter was measured by echo and comparison in survival was made.

In addition, the surviving animals were sacrificed after 28 days to analyze the AAA pathological tissue.

The AAA maximum short-axis diameter was measured with an ultrasonic diagnostic apparatus (Vevo770, manufactured by VisualSonics Inc.) on the day of operation and Day 7, Day 14, Day 21 and Day 28 post operation.

(5) Results

Figure 1:
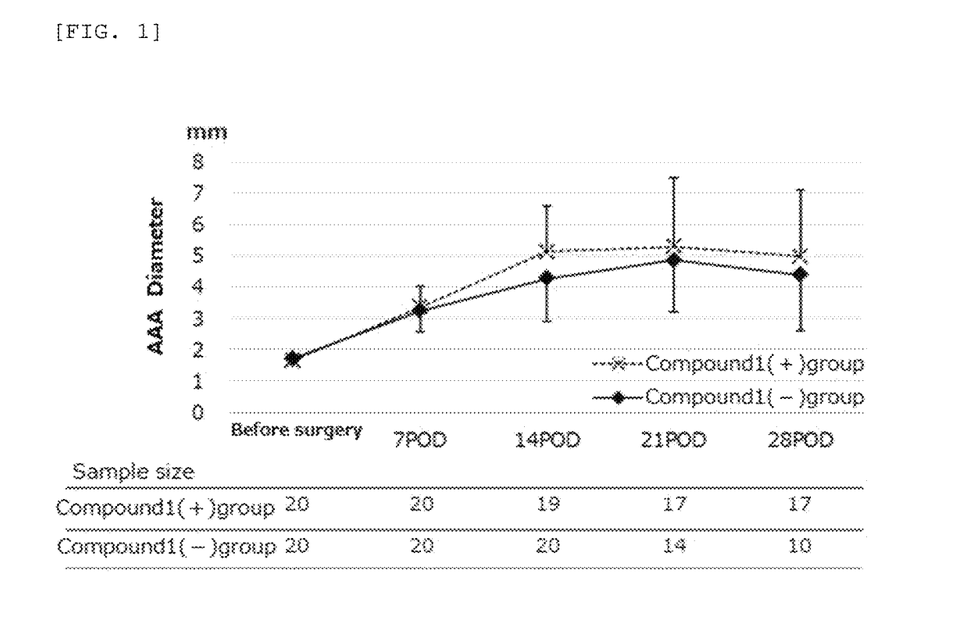
FIG. 1 shows the change of the aneurysm diameter (AAA maximum short-axis diameter) over days when an aortic wall hypoxia-induced rat AAA model was fed with a normal diet or Compound 1-mixed diet from 1 week before the AAA model creation operation (7 days before operation). The vertical axis indicates the aneurysm diameter, and the horizontal axis indicates the number of days elapsed after operation of AAA induction treatment (POD means postoperative days). ♦ is a plot of the mean value (mm) of the aneurysm diameter at each time point in a Compound 1 administration group (n=20). On the other hand, × is a plot of the mean value (mm) of the aneurysm diameter at each time point in a Compound 1 non-administration group (n=20). The sample size indicates survival cases at the time of measurement at each time point. No rat died by the measurement of the aneurysm diameter on Day 7 post operation, but the aneurysm diameter of the dead rats was not measured after Day 14 post operation. For this reason, the results after Day 14 post operation represent the mean value of the aneurysm diameter only for survival cases.

The measurement results of the aneurysm diameter are shown in FIG. 1.

Although there was no significant difference in the AAA diameter between the control (Compound 1 (−)) group and the Compound 1 (Compound 1 (+)) group, there was a tendency toward suppression of the increase in the aneurysm diameter in the Compound 1 group.

Figure 2:
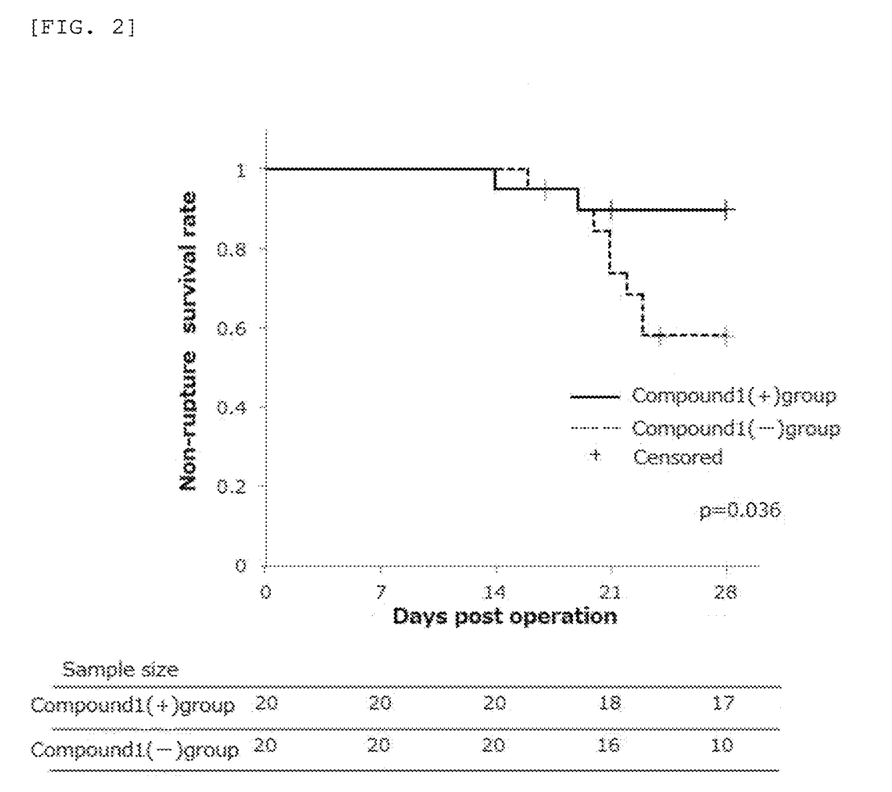
FIG. 2 shows the non-rupture survival rate when an aortic wall hypoxia-induced rat AAA model was fed with a normal diet or Compound 1-mixed diet from 1 week before the AAA model creation operation (7 days before operation). The vertical axis indicates the cumulative survival (the survival at the time of induction treatment of the aortic wall hypoxia-induced rat AAA model is 1.0), and the horizontal axis indicates the number of days elapsed after operation (the number of days elapsed after treatment with the induction treatment day being Day 0). The survival functions of the Compound 1 administration (Compound 1 (+)) group (n=20) and the Compound 1 non-administration (Compound 1 (−)) group (n=20) are shown. p=0.036 is a significant difference value obtained by testing the difference in non-ruptured survival between the administration group and the non-administration group by the Log Rank test. The sample size indicates survival cases at the start of each time point. Note that the sample size differs from that in FIG. 1 because of the presence of the cases which died by the measurement of the aneurysm diameter at each time point.

Next, the results of the non-rupture survival rate are shown in FIG. 2.

In the follow-up in a period from the day of operation to Day 28 post operation, the mortality due to rupture in the Compound 1 (Compound 1 (+)) group was significantly lower than that in the control (Compound 1 (−)) group (the p value by the Log Rank test was 0.036), i.e., the survival rate was significantly improved (one unexplained death case was found for the Compound 1 group and two unexplained death cases for the control group during the period, but all of the other death cases were confirmed, by autopsy, to be caused by AAA rupture).

Example 2: Action of Compound 1 in Aortic Wall Hypoxia-Induced Rat AAA Model (2)

In the same models as in Example 1, the effect of Compound 1 on the formed AAA was studied.

Specifically, the administration of the Compound 1-mixed diet was started one week after the AAA model creation operation (7 days after operation) until the end of the experiment in this example, in place of one week before the AAA model creation operation (7 days before operation) until the end of the experiment in Example 1 (3). In addition, on Day 7 post operation, rats having an aortic aneurysm diameter of 3 mm or more were selected by measurement with an ultrasonic diagnostic apparatus (Vevo770, manufactured by VisualSonics Inc.), and then the rats were randomly divided into two groups: a normal diet administration group (hereinafter referred to as "control group") (n=18) and a 0.15% Compound 1-mixed diet administration group (hereinafter referred to as "Compound 1 group") (n=15). The other conditions, i.e., the (1) test animal and rearing environment, (2) creation of aortic wall hypoxia-induced rat AAA model, (4) observation and inspection method, etc. in Example 1 were, in principle, the same as in Example 1.

Figure 3:
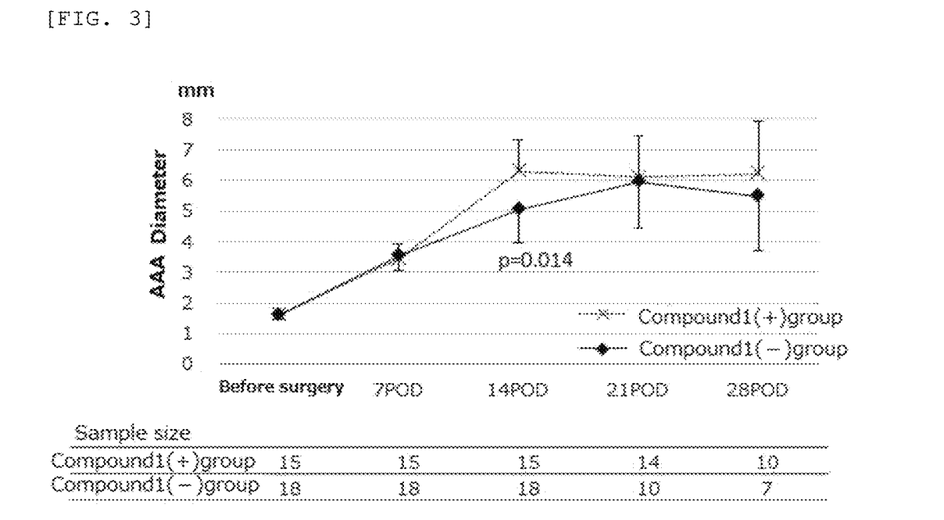
FIG. 3 shows the change of the aneurysm diameter (AAA maximum short-axis diameter) over days when an aortic wall hypoxia-induced rat AAA model was fed with a normal diet or Compound 1-mixed diet from one week after the AAA model creation operation (7 days after operation), wherein administration of the compound was started after confirmation of the formation of an aortic aneurysm. The vertical axis indicates the aneurysm diameter, and the horizontal axis indicates the number of days elapsed after operation of AAA induction treatment (POD means postoperative days). ♦ is a plot of the mean value (mm) of the aneurysm diameter at each time point in a Compound 1 administration group (n=15). On the other hand, × is a plot of the mean value (mm) of the aneurysm diameter at each time point in a Compound 1 non-administration group (n=18). p=0.014 is a significant difference value obtained by testing the difference in mean value of the aneurysm diameter between the administration group and the non-administration group in a period between D7 and D14 post operation by repeated measure analysis of variance. The sample size indicates survival cases at the time of measurement at each time point. No rat died by the measurement of the aneurysm diameter on Day 14 post operation, but the aneurysm diameter of the rats which died of aneurysm rupture was not measured after Day 21 post operation. For this reason, the results after Day 21 post operation represent the mean value of the aneurysm diameter only for survival cases.

The measurement results of the aneurysm diameter are shown in FIG. 3.

In a period from Day 7 to Day 14 post operation, the AAA diameter in the Compound 1 (Compound 1 (+)) group was significantly lower than that in the control (Compound 1 (−)) group (the p value by the Log Rank test was 0.014).), namely, the administration of Compound 1 suppressed the increase in the aneurysm diameter.

Figure 4:
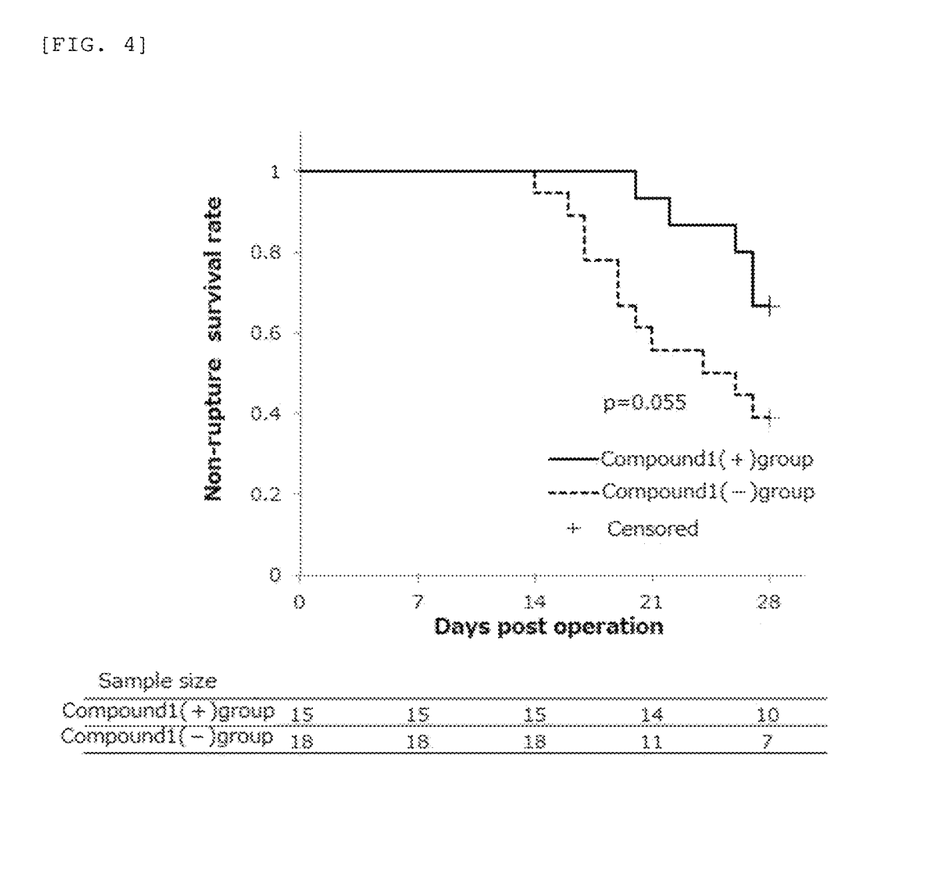
FIG. 4 shows the non-rupture survival rate when an aortic wall hypoxia-induced rat AAA model was fed with normal diet or Compound 1-mixed diet from one week after the AAA model creation operation (7 days after operation), wherein administration of the compound was started after confirmation of the formation of an aortic aneurysm. The vertical axis indicates the cumulative survival (the survival at the time of induction treatment of the aortic wall hypoxia-induced rat AAA model is 1.0), and the horizontal axis indicates the number of days elapsed after operation (the number of days elapsed after treatment with the induction treatment day being Day 0). The survival functions of the Compound 1 administration (Compound 1 (+)) group (n=15) and the Compound 1 non-administration (Compound 1 (−)) group (n=18) are shown. p=0.055 is a significant difference value obtained by testing the difference in non-ruptured survival between the administration group and the non-administration group by the Log Rank test. The sample size indicates survival cases at the start of each time point. Note that the sample size differs from that in FIG. 3 because of the presence of the cases which died of aneurysm rupture by the measurement of the aneurysm diameter at each time point.

Next, the results of the non-rupture survival rate are shown in FIG. 4.

In the follow-up in a period from the day of operation to Day 28 post operation, the mortality due to rupture in the Compound 1 (Compound 1 (+)) group was lower than that in the control (Compound 1 (−)) group (the p value by the Log Rank test was 0.055), namely, there was a tendency toward improvement in the survival rate upon administration of Compound 1 (all of the death cases were confirmed, by autopsy, to be caused by AAA rupture).

From the above results, it became clear that Compound 1 is extremely effective in suppressing the rupture and dilatation of AAA, and is extremely useful as a pharmaceutical composition for an aortic aneurysm, particularly, an agent for suppressing AAA rupture (drug for preventing AAA rupture) or an agent for suppressing AAA dilatation (drug for preventing AAA dilatation).

INDUSTRIAL APPLICABILITY

Compound 1 of the present invention is effective in suppressing rupture and/or dilatation of an aortic aneurysm and has industrial applicability as a compound that enables medical treatment for an aortic aneurysm.

The invention claimed is:

1. A method for treating an aortic aneurysm, comprising:
    administering an effective amount of (−)-6-[3-[3-cyclopropyl-3-[(1R,2R)-2-hydroxycyclohexyl]ureido] propoxy]-2(1H)-quinolinone or a salt thereof to a human subject in need of treatment,
    wherein the subject is a patient with an aortic aneurysm selected from the group consisting of abdominal aortic aneurysms, thoracoabdominal aortic aneurysms, and thoracic aortic aneurysms.

2. The method according to claim 1, wherein the treatment of the aortic aneurysm includes at least one treatment selected from the group consisting of suppression of aneurysm rupture, suppression of aneurysm dilatation, and aneurysm size reduction.

3. The method according to claim 2, wherein the treatment of the aortic aneurysm is suppression of aortic aneurysm rupture.

4. The method according to claim 2, wherein the treatment of the aortic aneurysm is suppression of aortic aneurysm rupture after endovascular stent-grafting.

5. The method according to claim 2, wherein the treatment of the aortic aneurysm is suppression of aortic aneurysm rupture before endovascular stent-grafting or aortic aneurysmectomy.

6. The method according to claim 2, wherein the treatment of the aortic aneurysm is suppression of aortic aneurysm dilatation.

7. The method according to claim 2, wherein the treatment of the aortic aneurysm is suppression of aortic aneurysm dilatation after endovascular stent-grafting.

8. The method according to claim 2, wherein the treatment of the aortic aneurysm is suppression of aortic aneurysm dilatation before endovascular stent-grafting or aortic aneurysmectomy.

9. The method according to claim 2, wherein the treatment of the aortic aneurysm is aortic aneurysm size reduction.

10. The method according to claim 1, wherein the subject is a patient with abdominal aortic aneurysm.

11. The method according to claim 2, wherein the subject is a patient with abdominal aortic aneurysm.

12. A method for suppressing aortic aneurysm rupture, comprising:
    administering an effective amount of (−)-6-[3-[3-cyclopropyl-3-[(1R,2R)-2-hydroxycyclohexyl]ureido] propoxy]-2(1H)-quinolinone or a salt thereof to a human subject in need of treatment,
    wherein the subject is a patient with an abdominal aortic aneurysm.

13. A method for suppressing aortic aneurysm dilatation, comprising:
    administering an effective amount of (−)-6-[3-[3-cyclopropyl-3-[(1R,2R)-2-hydroxycyclohexyl]ureido] propoxy]-2(1H)-quinolinone or a salt thereof to a human subject in need of treatment,
    wherein the subject is a patient an abdominal aortic aneurysm.

14. The method of claim 1, undertaken before endovascular stent-grafting or aortic aneurysmectomy.

15. The method of claim 12, undertaken before endovascular stent-grafting or aortic aneurysmectomy.

16. The method of claim 13, undertaken before endovascular stent-grafting or aortic aneurysmectomy.

17. The method of claim 1, wherein the effective amount is from 25 mg/day to 200 mg/day.

18. The method of claim 12, wherein the effective amount is from 25 mg/day to 200 mg/day.

19. The method of claim 13, wherein the effective amount is from 25 mg/day to 200 mg/day.

20. The method of claim 14, wherein the effective amount is from 25 mg/day to 200 mg/day.

21. The method of claim 15, wherein the effective amount is from 25 mg/day to 200 mg/day.

22. The method of claim 16, wherein the effective amount is from 25 mg/day to 200 mg/day.

* * * * *